United States Patent [19]
Grove

[11] Patent Number: 5,303,310
[45] Date of Patent: Apr. 12, 1994

[54] METHOD AND APPARATUS FOR IMAGE ANALYSIS OF COMPOSITE ORES

[75] Inventor: Richard D. Grove, Lakeland, Fla.

[73] Assignee: IMC Fertilizer, Inc., Northbrook, Ill.

[21] Appl. No.: 753,348

[22] Filed: Aug. 30, 1991

[51] Int. Cl.$^5$ ............ G06K 9/00; G06K 9/46; G01N 21/00; H04N 7/18
[52] U.S. Cl. .............................. 382/8; 382/18; 382/23; 382/1; 356/432; 348/142
[58] Field of Search ........... 382/1, 18, 8, 28, 23, 382/51; 356/432; 358/100, 107; H04N 7/18

[56] References Cited

U.S. PATENT DOCUMENTS

| 2,494,441 | 1/1950 | Hillier | 250/19.5 |
|---|---|---|---|
| 2,536,693 | 1/1951 | Okolicsanyi | 209/3.2 |
| 2,707,555 | 5/1955 | Gaudin | 209/72 |
| 3,011,634 | 12/1961 | Hutter et al. | 209/74 |
| 3,052,353 | 9/1962 | Pritchett | 209/111.5 |
| 3,053,388 | 9/1962 | Tittle | 209/111.5 |
| 3,305,089 | 2/1967 | Fraenkel | 209/111.6 |
| 3,356,211 | 12/1967 | Mathews | 209/9 |
| 3,395,793 | 8/1968 | Thompson et al. | 209/3.3 |
| 3,472,375 | 10/1969 | Mathews | 209/111.5 |
| 3,617,631 | 11/1971 | Soames | 178/6.8 |
| 3,705,318 | 12/1972 | Frayer | 382/18 |
| 3,746,265 | 7/1973 | Dancy | 241/20 |
| 3,791,744 | 2/1974 | Erny et al. | 356/432 |
| 3,936,188 | 2/1976 | Sawyer | 356/36 |
| 3,962,403 | 6/1976 | Wyslouzil | 423/206 |
| 3,977,526 | 8/1976 | Gordon et al. | 209/111.7 |
| 4,064,534 | 12/1977 | Chen et al. | 358/107 |
| 4,088,552 | 5/1978 | Morrison et al. | 204/157.1 |
| 4,122,952 | 10/1978 | Richards | 209/579 |
| 4,136,950 | 1/1979 | Labrum et al. | 356/28 |
| 4,140,601 | 2/1979 | Gomberg | 204/157.1 |
| 4,169,045 | 9/1979 | Moudgil et al. | 209/3.3 |
| 4,204,950 | 5/1980 | Burford, Jr. | 209/558 |
| 4,210,311 | 7/1980 | Stone | 251/129 |
| 4,231,478 | 11/1980 | Stone | 209/576 |
| 4,266,675 | 5/1981 | Barwise et al. | 209/540 |
| 4,361,238 | 11/1982 | Kealy et al. | 209/576 |
| 4,371,265 | 2/1983 | Mitsuhashi | 356/432 |
| 4,462,495 | 7/1984 | McKinley et al. | 209/3.3 |
| 4,532,545 | 7/1985 | Hanson | 358/100 |
| 4,561,018 | 12/1985 | Berthel et al. | 358/107 |
| 4,592,082 | 5/1986 | Pawloski | 378/75 |
| 4,617,682 | 10/1986 | Mori et al. | 382/28 |
| 4,629,709 | 12/1986 | Cofler et al. | 502/5 |
| 4,814,868 | 3/1989 | James | 358/100 |
| 4,918,739 | 4/1990 | Lorente et al. | 382/1 |
| 4,965,841 | 10/1990 | Kaneko et al. | 382/1 |
| 5,011,595 | 4/1991 | Meenan et al. | 209/166 |

FOREIGN PATENT DOCUMENTS 1212357 10/1986 Canada ............ B03B 1/00

OTHER PUBLICATIONS

*Beneficiation at Large Particle Size Using Photometric Sorting Techniques*, Mark A. Schapper, Ph.D., M.Sc., Australian Mining, May 1977.
*Selection and Sizing of Ore Sorting Equipment*, A. M. Stone, Chapter, 17, pp. 261-267.
*Industrial Minerals Beneficiation By Ore Sorting*, Bo R. Arvidson, Ph.D., Ore Sorters (North America) Inc., pp. 1-11.

Primary Examiner—Leo H. Boudreau
Assistant Examiner—Michael Cammarata
Attorney, Agent, or Firm—Banner, Birch, McKie & Beckett

[57] ABSTRACT

The relative concentration of opaque and translucent ore particles is determined by illuminating a falling stream of particles with a source of backlighting which provides a diffused background light source for detecting opaque particles and a relatively brighter light source for further illuminating translucent particles. Scanning a captured image of the falling particle stream for light and dark light images relative to the background light permits the relative concentration of opaque and translucent particles to be determined. The method is particularly useful for beneficiated composite phosphate ores containing desirable opaque phosphate particles and undesired translucent quartz particles.

10 Claims, 1 Drawing Sheet

METHOD AND APPARATUS FOR IMAGE ANALYSIS OF COMPOSITE ORES

TECHNICAL FIELD

This invention relates to a method and apparatus for image analysis of composite ores. Specifically, a method and apparatus to determine the relative concentrations of translucent and opaque components in composite ore are provided.

BACKGROUND OF THE INVENTION

Process control of flotation beneficiation of composite ores often is based on the relative concentrations of particulate translucent and opaque components in the ore. Typically, these concentrations are visually estimated by plant operators. It is widely recognized that because such estimates are subjective, they therefore vary from operator to operator. Also, such subjective estimates are imprecise and inaccurate.

Various methods and apparatus for the image analysis of particles are known. For example, U.S. Pat. No. 4,136,950 discloses a microscope system for observation of small particles in motion, such as particles emanating from an aerosol container. A video camera is used to observe the particles through stop action photography by the use of strobe lighting to create an image. The image then is stored in a short-term memory. The stored image is converted to electrical image-information signals by scanning the camera's imaging device, in accordance with the conventional operation of such a camera. The patent further discloses use of a 'shading corrector' positioned in front of the camera to correct differences in background brightness and ensure that the background appears uniformly bright.

U.S. Pat. No. 4,617,682 discloses an apparatus and method for automatic quantitative measurement by image analysis of textures of optically anisotropic material having a known anisotropic nature. In particular, the patent is directed to quantitative analysis of coke. In accordance with the method of this patent, extensive sample preparation is required. The anisotropic material, for example, coke particles, is imbedded in resin visually distinct from the material. The reflectance pattern of the coke-containing resin is viewed through a polarizing microscope. The pattern is stored as grayscale information from an image divided into pixels; the resin has a grayscale value lower than that of the coke. Differences between grayscales of a base set of pixels and grayscales of subsets of pixels surrounding the base set of pixels are determined. The reflectance patterns are determined from these differences by comparison to pre-determined differences corresponding to the various textures (i.e., anisotropic areas) of the coke. Grayscales lower than those of the coke, which indicate that the primary component detected by the pixel is resin, are eliminated from consideration by pre-established criteria. Use of this method is burdensome, and requires mounting of the particles in resin.

U.S. Pat. No. 4,561,018 discloses an apparatus for viewing particulate matter, especially snow and other solid hydrometers. Particles are moved into the field of view of the camera, where motion of the image can be stopped by a strobe lamp.

U.S. Pat. No. 4,814,868 discloses an apparatus and a method for identifying moving particles by filtering image information to eliminate not only 'noise' but also stationary objects and variations in the background.

The subject invention provides an apparatus and method for the image analysis of composite ores, whereby the relative concentrations of translucent and opaque components are reliably, accurately, and quickly determined. More specifically, the subject invention provides an apparatus and method for the image analysis of phosphate ore, whereby the relative concentrations of phosphate and quartz are determined.

SUMMARY OF THE INVENTION

The present invention provides an apparatus and a method to determine the relative concentrations of translucent and opaque components of a flowing stream of composite ore. In the apparatus, sources of light are placed not only to "stop" the motion of a flowing composite ore stream to permit the camera to view the stream, but also to provide information from which the relative concentrations can be determined.

The apparatus comprises a camera capable of capturing an image comprising a matrix of pixels, each pixel containing a grayscale value of incident light. A composite ore stream is allowed to flow generally perpendicularly past the viewing plane of the camera. An iris is placed between the sample plane and the camera, with two light sources on the side opposite the sample plane from the camera. Together with a diffuser, these light sources illuminate the sample plane to produce the image, which is stored by the camera. The stored image is analyzed to determine the relative concentrations of translucent and opaque components of the composite ore.

The present invention also provides a method for determining the relative concentrations of translucent and opaque components of a composite ore reliably, accurately, and quickly. The composite ore is allowed to flow generally perpendicularly past the viewing plane of a video camera. Light sources on the side opposite the sample project light through the sample as it flows past the camera. One light provides background illumination; the other, in conjunction with the first, "stops" the action to form an image in the camera. The image is stored as grayscale pixel data. The stored image is then scanned to determine the relative concentrations of translucent and opaque components of the composite ore. The method is useful in process control of, for example, beneficiation of mineral-containing ores.

DETAILED DESCRIPTION OF THE INVENTION

Figure 1:
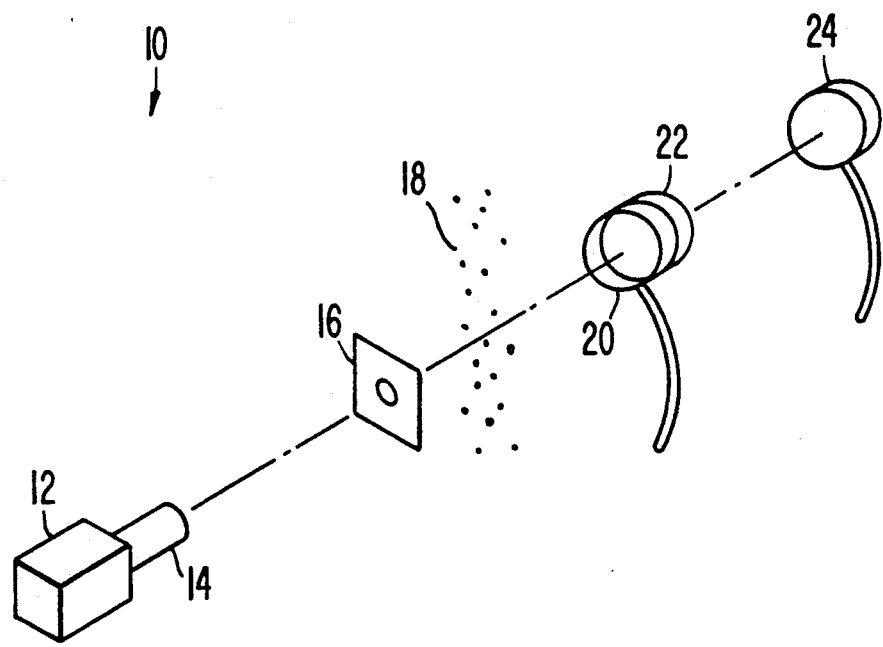
FIG. 1 represents the apparatus of the invention.

This invention is based on the discovery that the relative concentrations of the principal constituent of a solid particulate composition can be determined quickly, easily, and accurately. It has been discovered that the relative concentrations of the principal constituents of a particulate solid which have different light transmission properties can be determined by backlighting, in accordance with the description herein, a stream of the solids flowing past a camera and analyzing the image thereof.

In particular, the invention is described herein with respect to phosphate ore. In such ore, the phosphate constituent is opaque and the quartz impurities are translucent and have multifaceted surfaces which transmit and refract light. Analysis of an image generated by backlighting in accordance with the description herein provides the relative concentrations of constituents.

Determination of the relative component concentrations in such ores can be used in the control of, for example, a process for beneficiation of such ore. For example, flotation beneficiation of phosphate-containing ore could be controlled by determining the relative concentration of phosphate and quartz particles in either the feed to or effluent from a flotation cell (particles with a size of about 10–65 mesh, i.e., about 0.15–0.81 mm) and using the inventive analysis method to adjust the operation of that cell.

The invention is directed to a method and apparatus for determination of the relative concentrations of opaque and translucent constituents of a composite ore by perceiving the differences in optical properties of the principal solid constituents. The principal solid constituents of the composite ore are translucent and opaque. More specifically, the invention takes advantage of the different optical properties of the solid constituents of phosphate ore: phosphate mineral (principally francolite) and quartz. In general phosphate mineral is opaque, whereas quartz is translucent. Additionally, quartz particles typically have multi-faceted surfaces which refract and reflect light in a multitude of directions.

The drawing depicts apparatus of the invention. More particularly, FIG. 1 depicts by way of illustration, but not of limitation, an image analysis apparatus 10 according to the present invention.

The image analysis apparatus 10 comprises a video camera 12 with lens 14, iris 16, first illuminator 20, diffuser 22, and second illuminator 24.

The apparatus' components typically are mounted in a light-tight box with the video camera 12 and lens 14 pointed generally horizontally toward a generally vertically falling sample 18. The first and second illuminators 20 and 24 are positioned behind (i.e., on the opposite side of the sample from video camera 12 and lens 14) the vertically falling sample 18. First illuminator 20 is positioned closer to the sample 18 than the second illuminator 24. The diffuser 22 is positioned between the first and second illuminators 20 and 24. Iris 16 is positioned between the video camera 12 and vertically falling sample 18.

In use, a sample of composite ore is caused to fall in an approximate monolayer in a vertical plane perpendicular to the surface of the video camera lens 14. The first and second illuminators 20 and 24 are triggered to flash, thus allowing capture of an image of the falling sample 18 by the video camera 12, essentially without dimensional distortion caused by the motion of the falling sample stream.

The second illuminator 24 projects light onto the surface of the diffuser 22. The diffuser 22 transmits uniform background lighting approximately at the midrange of the grayscale of the video system. The uniform background light transmitted by the diffuser 22 projects onto the lens 14 by passing through interstices between the particles of falling sample 18. The opaque particles are thereby recorded as dark spots by the video camera 12.

The components of the apparatus of the present invention are arranged such that the diameter of the cone of acceptance of the video camera lens 14 at the sample plane is smaller than the diameter of the cone of projection of the first illuminator 20. Thereby, the majority of light from the first illuminator 20 is prevented from directly entering lens 14, and the spacial relationship of components permits the camera to capture a full view of the sample without edge effects. The iris 16 is positioned between the lens 14 and the falling sample 18 to augment and control this effect.

A small portion of light from first illuminator 20 would, in the absence of the iris, enter the video camera lens 14 at a narrow angle. Iris 16 is positioned to block light at that angle while not obstructing the camera field of view. Skilled practitioners realize that the shape of the iris 16 and its distance from the lens can be varied to achieve the desired effect. In an embodiment of the invention as set forth in FIG. 1, the inner diameter of a round iris 16 is slightly larger than the diagonal of the camera field of view.

The position, i.e., the distance from the lens, of iris 16 can be established by masking the second illuminator 24 and then taking a picture of a blank field illuminated only by first illuminator 20. The iris 16 is moved along a line between the sample plane and the camera lens until the resulting video picture shows no illumination. Skilled practitioners thus are able to establish the correct position of the lens in accordance with these guidelines. Preferably, the first illuminator 20 is a fiber optic ring illuminator.

In one embodiment of the invention the second illuminator 24 is a fiber optic ring illuminator. In a preferred embodiment of the invention the second illuminator 24 is a fiber optic flat pack which provides an inexpensive source of uniform light. Such a fiber optic flat pack incorporates diffuser 22. Thus, a separate diffuser is not necessary when a fiber optic flat pack is utilized.

First illuminator 20 projects light which is brighter than that projected by the second illuminator 24 onto the falling sample 18 generally toward the camera 12. However, light from first illuminator 20 is projected at a low angle referenced to the vertical plane of the falling sample 18, such that the majority of light from the first illuminator 20 will not directly enter lens 14. Preferably, no light from first illuminator 20 directly enters lens 14. The translucent particles which form at least a part of falling sample 18, however, allow entrance of light from many angles and provide transmission of light in many directions, thereby projecting the relatively bright light from the first illuminator 20 into the lens 14 and camera 12. Thus, bright spots representing the translucent particles are recorded by the video camera 12. In particular, the translucent particles are quartz and the opaque particles are phosphate particles present in a composite phosphate ore.

Light from first illuminator 20 is brighter than that from second illuminator 24 because diffuser 22, mounted in front of the second illuminator 24, scatters light which strikes it. Therefore, the light intensity of second illuminator 24 is reduced relative to the light intensity of undiffused first illuminator 20.

The illuminators 20 and 24 are operated in conjunction as flashbulbs to enable stop-action photography by the video camera. The video camera is equipped with a remote controller which decodes the accompanying video camera scanning signal to provide a field identification marker. The positive transition of the field marker marks the beginning of frame accumulation, and the illuminators are fired, or flashed, at the beginning of frame accumulation. In this way, all areas of the frame are illuminated.

Therefore, illumination of the illuminators 20 and 24 is synchronized with operation of the video camera by a switch. The switch acts to "flash" the illuminators 20 and 24 at the beginning of a new frame in the video camera 12, thus providing a video frame in which only one image of the vertically falling sample 18 is depicted and ensuring that one frame contains all information. Switching mechanisms which permit synchronized flashing of illuminators with the field marker of a camera are known to skilled practitioners in the art.

The video camera 12 captures the image as a matrix of picture elements (pixels), which is transferred to an imaging memory. A standard video camera image comprises 240,000 pixels. However, any number of pixels which provides the desired matrix of information is suitably used in the invention.

The matrix information transferred to the imaging memory includes one grayscale value for each pixel. The grayscale used with the subject invention typically contains 256 values: 0 being black and 255 being white. However, any grayscale can be used with the subject invention, recognizing of course, that a grayscale having fewer gradations yields poorer resolution (i.e. less accuracy).

The grayscale values of the pixels which comprise the frame are stored in an imaging memory and are categorized into three bands or ranges. The range below a pre-determined limit value is considered to encompass dark areas which indicate the presence of opaque materials, such as phosphate mineral. The range above a second, brighter, predetermined threshold value is considered to represent bright areas projected by translucent materials, such as quartz particles. Intermediate grayscale values, i.e., those between the two threshold values, are not of interest because they merely represent the diffuse background lighting projected by the second illuminator 24.

The number of pixels, or the areas of the pixels, having grayscale values in the 'dark' and 'bright' ranges, respectively, are used to determine the quantity of opaque and translucent components, respectively, in the sample. The limit grayscale value for the dark band representing the opaque material, such as phosphate mineral, is typically about 130. That is, grayscales from 0 to about 130 represent opaque material in such phosphate ore. The threshold grayscale value for the bright band representing the translucent material, such as quartz, is typically about 210. Thus, grayscales from about 210 to 255 represent translucent material such as quartz. The intermediate grayscale values, i.e., those from about 130 to about 210 represent the diffuse background lighting. Skilled practitioners in the art recognize that the threshold grayscale values for other composite ores will vary, and can be determined in accordance with the guidelines set forth herein.

The concentration of phosphate mineral and quartz in the sample can be calculated based on the number of areas of the pixels having grayscale values in the 'dark' and 'bright' ranges. In particular, relationships derived by regression analysis can be used to determine the concentrations based on the area of each of the components of the sample.

Alternatively, it can be assumed that all particles analyzed are spheroids, so that, as a row is scanned, any continuum of pixels falling in either the upper or lower band represents a diameter of the respective particle. For example, if a continuum of 30 pixels were found when scanning a particular row, the volume of a spheroid section or disk of diameter equivalent to 30 pixels would be included in the summation of all disk volumes falling in the appropriate range. This measure could be used to estimate the volume of opaque or translucent material in the sample by the following formula:

$$V = \Sigma(\pi/4)d^2 h$$

wherein, V represents the constituent volume, and d is the individual disk diameter. The height of the disks, h, can be considered a dimensional constant that scales the camera sensor dimensions to the camera field of view.

In one particular embodiment of this invention, 500 pixel columns are mapped to about 16 millimeters in the sample plane. Because the individual pixels are square, mapping the 500 pixels to a 16 millimeter sample means that each pixel represents a length and width of about 32 microns in the camera field of view. Other mapping arrangements can be made. Density constants for the respective minerals then can be used to convert the estimated volumes to estimated weights. Skilled practitioners are familiar with such mapping and density/volume interconversions.

Typically, flashing of the illuminators, storing of the pixels to create a matrix of grayscale values, and scanning of the captured matrices are repeated to obtain an acceptable average of concentration values. It is preferred that about 8 pixel matrices be obtained and analyses thereof be carried out for each determination of relative component concentrations in a stream.

The following examples are for illustrative purposes only and are not meant to limit the claimed invention in any manner.

EXAMPLES

Fifteen samples each of two phosphate ore flotation streams from a commercial phosphate flotation beneficiation plant were sampled. The two streams sampled were the course rougher flotation feed stream and the amine tailings stream. Thus, the former stream is comprised of the course rougher phosphate feed particles whereas the latter stream is comprised of finer phosphate particles and has a lower concentration of phosphate and a higher concentration of quartz than the former stream. The samples were analyzed by image analysis according to the present invention, as well as by standard chemical methods.

The image analysis of the phosphate ore flotation stream comprised capturing an image of the sample stream, storing the captured image and scanning the stored matrix to determine the relative concentrations of phosphate and quartz in the stream. The results generated by the analysis of the present invention were compared to the results obtained by conventional wet chemical analysis. The results were compared using an accepted measure of the phosphate mineral content of phosphate ore, percent BPL (base phosphate of lime), and an accepted measure of the quartz content, percent insol (dry weight percentage of acid insoluble material in the sample). Regression analysis then was conducted to derive equations to formulate the basis for determining the concentration of phosphate and quartz in the stream analyzed, the results of which formed the basis for the comparison.

The apparatus used to obtain the images for analysis included a GP-CD60 Panasonic Solid State Video Camera with a Nikkor 55 mm Macro F/2.8 lens with a lens adapter (C adapter). The end of the video camera opposite the lens was utilized as a reference plane for distances. The distance from the end of the camera to the tip of the lens was approximately 315 mm. An iris was placed approximately 65 mm from the lens (i.e., about 380 mm from the reference plane). The iris was made by forming a 30 mm hole in cardboard and mounting the cardboard iris on a filter holder.

The sample plane was about 100 mm from the lens (about 415 mm from the reference plane). A first ring illuminator was placed about 155 mm from the lens (about 470 mm from the reference plane). A 76 mm diameter opal diffuser was glued to the back of the first illuminator, thus placing the diffuser approximately 180 mm from the lens (495 mm from the reference plane). A second ring illuminator was placed approximately 260 mm from the lens (575 mm from the reference plane). Each illuminator was a B38,296 Ring Illuminator Light Guide from Edmond Scientific Company.

Because neither illuminator contained its own source of light, the flash components was obtained from a Vivatar 285 HV Flash and a Vivatar SB-4 adapter. The flash was mounted to the inside of a plastic enclosure door of an aluminum box so that the flash output faced the door. Two 12 mm diameter holes were drilled through both the aluminum box and the plastic enclosure door where the flash was mounted. The ends of the two illuminators were then press fit into the holes. Thus, the ring light guides received light from the flash and became illuminated.

The video camera was focused at 0.25 meters with the aperture set at f/16. The approximate magnification was 10× so that each pixel was mapped to approximately 32 microns of the sample in the video camera field of view. An AVC-1Plus Advanced Videographic Controller Board Set was used to control the image analysis apparatus. Data was analyzed in a micro computer.

A Model F-T0 electromagnetic vibrating feeder with stainless steel trough was used to feed the sample to the image analysis apparatus. Vibration of the trough was controlled by a SCR-1B phase angle controller. The feed rate could therefore be computer controlled by adding an interface to the controller. The feeder trough was mounted so that the main body of the feeder was below the camera lens and the trough was above the camera lens.

For a sample size of approximately 300 grams, the time for image analysis was about 2 minutes, 30 seconds.

For Tables I and II of Examples 1 and 2 the following abbreviations apply.

| | |
|---|---|
| LB PIX | Pixels with membership in the lower band |
| UB PIX | Pixels with membership in the upper band |
| INS A | Percent insol by wet chemistry, i.e., % quartz |
| BPL A | Percent BPL (bone phosphate of lime) by wet chemistry |
| INS B | Percent insol by Equation 1 below |
| INS C | Percent insol by Equation 3 below |
| INS B-A, C-A | Insol by image analysis minus insol by wet chemistry |
| BPL B | Percent BPL by Equation 2 below |
| BPL C | Percent BPL by Equation 4 below |
| BPL B-A, C-A | BPL by image analysis minus BPL by wet chemistry) |

EXAMPLE 1

Example 1 represents the results obtained when the image analysis information was converted to quartz and phosphate concentrations by the following regression analysis-derived equations based on the image analysis percent area measurement, and wet chemistry analyses:

$$INS\ B = 14.04 + 0.7027\ (A) \qquad \text{EQUATION 1}$$

$$BPL\ B = 65.24 - 0.5565\ (A) \qquad \text{EQUATION 2}$$

wherein, INS B is the percent insolubles (quartz), BPL B is the percent phosphate, and A is the percent of pixels with grayscale values in the upperband. The results of the image analysis, the regression analysis and the concentration determined by wet chemistry are displayed in Table I.

TABLE I

IMAGE ANALYSIS AREA METHOD VERSUS WET CHEMISTRY

| SAMPLE | LB PIX | UB PIX | INS A | INS B | INS B-A | BPL A | BPL B | BPL B-A |
|---|---|---|---|---|---|---|---|---|
| 1 | 29459 | 98668 | 66.29 | 68.15 | 1.86 | 22.49 | 22.39 | −.10 |
| 2 | 11667 | 162012 | 76.37 | 79.59 | 3.22 | 14.85 | 13.33 | −1.52 |
| 3 | 19345 | 92401 | 69.78 | 72.15 | 2.37 | 20.45 | 19.22 | −1.23 |
| 4 | 29708 | 91064 | 66.02 | 67.02 | 1.00 | 26.88 | 23.28 | −3.60 |
| 5 | 23938 | 92704 | 74.44 | 69.89 | −4.55 | 21.43 | 21.01 | −.42 |
| 6 | 24565 | 96579 | 75.83 | 70.06 | −5.77 | 17.00 | 20.87 | 3.87 |
| 7 | 18418 | 86752 | 75.69 | 72.00 | −3.69 | 16.98 | 19.34 | 2.36 |
| 8 | 19278 | 75074 | 69.79 | 69.95 | .16 | 20.29 | 20.96 | .67 |
| 9 | 30245 | 98407 | 67.11 | 67.79 | .68 | 24.47 | 22.67 | −1.80 |
| 10 | 25132 | 73000 | 65.61 | 66.31 | .70 | 25.35 | 23.84 | −1.51 |
| 11 | 30019 | 87654 | 64.71 | 66.38 | 1.67 | 23.69 | 23.79 | .10 |
| 12 | 23002 | 89589 | 70.36 | 69.95 | −.41 | 21.38 | 20.96 | −.42 |
| 13 | 28590 | 76006 | 65.07 | 65.18 | −.03 | 23.07 | 24.80 | 1.73 |
| 14 | 29126 | 88813 | 62.47 | 66.96 | 4.49 | 24.42 | 23.33 | −1.09 |
| 15 | 24179 | 87424 | 70.98 | 69.09 | −1.89 | 18.74 | 21.65 | 2.91 |

EXAMPLE 2

Example 2 represents the results obtained when the image analysis information was converted to quartz and phosphate concentrations by the following regression analysis-derived equations based on the image analysis percent area estimates, and wet chemistry analyses:

$$INS\ C = -14.16 + 1.0541\ (A) \qquad \text{EQUATION 3}$$

$$BPL\ C = 81.89 - 0.7024\ (A) \qquad \text{EQUATION 4}$$

wherein, INS C is the percent insolubles (quartz), BPL C is the percent phosphate, and A is the percent of pixels with grayscale values in the upperband. The results are displayed in Table II.

TABLE II
IMAGE ANALYSIS AREA METHOD VERSUS WET CHEMISTRY

| SAMPLE | LB PIX | UB PIX | INS A | INS C | INS C-A | BPL A | BPL C | BPL C-A |
|---|---|---|---|---|---|---|---|---|
| 1 | 9136 | 115327 | 81.71 | 83.51 | 1.80 | 13.23 | 11.25 | −1.98 |
| 2 | 6258 | 125208 | 87.61 | 86.23 | −1.38 | 9.00 | 9.28 | .28 |
| 3 | 12360 | 82965 | 77.34 | 77.58 | .24 | 15.71 | 15.54 | −.17 |
| 4 | 11440 | 101856 | 78.40 | 80.61 | 2.21 | 12.78 | 13.35 | .57 |
| 5 | 7927 | 92265 | 85.13 | 82.91 | −2.22 | 9.89 | 11.68 | 1.79 |
| 6 | 5732 | 83374 | 88.77 | 84.47 | −4.30 | 6.32 | 10.55 | 4.23 |
| 7 | 12202 | 76358 | 77.28 | 76.73 | −.55 | 15.83 | 16.15 | .32 |
| 8 | 4264 | 82093 | 87.47 | 86.05 | −1.42 | 9.16 | 9.41 | .25 |
| 9 | 5931 | 99406 | 84.14 | 85.31 | 1.17 | 10.80 | 9.94 | −.86 |
| 10 | 7465 | 65671 | 81.06 | 80.49 | −.57 | 14.40 | 13.43 | −.97 |
| 11 | 7041 | 77662 | 85.96 | 82.49 | −3.47 | 10.51 | 11.99 | 1.48 |
| 12 | 5280 | 89429 | 85.32 | 85.37 | .85 | 11.04 | 9.90 | −1.14 |
| 13 | 6854 | 84368 | 79.60 | 83.33 | 3.73 | 13.54 | 11.38 | −2.16 |
| 14 | 7369 | 106818 | 80.77 | 84.45 | 3.68 | 12.85 | 10.57 | −2.28 |
| 15 | 4974 | 114861 | 85.71 | 86.87 | 1.16 | 8.10 | 8.81 | .71 |

For Tables III and IV of Examples 3 and 4 of the following abbreviations apply.

| | |
|---|---|
| LB VOL | Volume estimate of particles mapped to lower band |
| UB VOL | Volume estimate of particles mapped to upper band |
| INS A | Percent insol by wet chemistry, i.e., % quartz |
| BPL A | Percent BPL (bone phosphate of lime) by wet chemistry |
| INS B | Percent insol by equation 5 below |
| INS C | Percent insol by equation 7 below |
| INS B-A, C-A | Insol by image analysis minus insol by wet chemistry |
| BPL B | Percent BPL by equation 6 below |
| BPL C | Percent BPL by equation 8 below |
| BPL B-A, C-A | BPL by image analysis minus BPL by wet chemistry |

EXAMPLE 3

Example 3 represents the results obtained when the image analysis information was converted to quartz and phosphate concentrations by the following regression analysis-derived equations, based on image analysis volume estimates, and wet chemistry analyses:

$$INS\ B = 38.19 + 0.4512\ (B) \quad \text{EQUATION 5}$$

$$BPL\ B = 47.13 - 0.3720\ (B) \quad \text{EQUATION 6}$$

wherein, INS B and BPL B are as indicted above, and B is the percent weight of particles mapped to the upper band. The results are displayed in Table III.

TABLE III
IMAGE ANALYSIS VOLUME WEIGHT METHOD VERSUS WET CHEMISTRY

| SAMPLE | LB VOL | UB VOL | INS A | INS B | INS B-A | BPL A | BPL B | BPL B-A |
|---|---|---|---|---|---|---|---|---|
| 1 | 400547 | 812952 | 66.29 | 67.33 | 1.04 | 22.49 | 23.11 | .62 |
| 2 | 96627 | 1090552 | 76.37 | 79.26 | 2.89 | 14.85 | 13.27 | −1.58 |
| 3 | 228089 | 666687 | 69.78 | 78.87 | 1.09 | 20.45 | 20.19 | −.26 |
| 4 | 359376 | 736688 | 66.02 | 67.43 | 1.41 | 26.88 | 23.02 | −3.86 |
| 5 | 379070 | 812078 | 74.44 | 67.88 | −6.56 | 21.43 | 22.65 | 1.22 |
| 6 | 308587 | 836595 | 75.83 | 70.18 | −5.65 | 17.00 | 20.76 | 3.76 |
| 7 | 185134 | 576478 | 75.69 | 71.43 | −4.26 | 16.98 | 19.73 | 2.75 |
| 8 | 194796 | 520696 | 69.79 | 70.04 | .25 | 20.29 | 20.87 | .58 |
| 9 | 381583 | 825243 | 67.11 | 67.98 | .87 | 24.47 | 22.57 | −1.98 |
| 10 | 248910 | 615442 | 65.61 | 69.30 | 3.69 | 25.35 | 21.48 | −3.87 |
| 11 | 460647 | 809036 | 64.71 | 65.81 | 1.10 | 23.69 | 24.36 | .67 |
| 12 | 288166 | 715597 | 70.36 | 69.35 | −1.01 | 21.38 | 21.44 | .06 |
| 13 | 344454 | 657863 | 65.07 | 66.70 | 1.63 | 23.07 | 23.63 | .56 |
| 14 | 422842 | 782425 | 62.47 | 66.36 | 3.89 | 24.42 | 23.90 | −.52 |
| 15 | 294359 | 823400 | 70.98 | 70.47 | −.51 | 18.74 | 20.52 | 1.78 |

EXAMPLE 4

Example 4 represents the results obtained when the image analysis information was converted to quartz and phosphate concentrations by the following regression analysis-derived equations based on image analysis volume estimates, and wet chemistry analyses:

$$INS\ C = 2.16 + 0.8794\ (B) \quad \text{EQUATION 7}$$

$$BPL\ C = 71.85 - 0.6553\ (B) \quad \text{EQUATION 8}$$

wherein, INS C and BPL C are as indicted above. The results are displayed in Table IV.

TABLE IV
IMAGE ANALYSIS VOLUME/WEIGHT METHOD VERSUS WET CHEMISTRY

| SAMPLE | LB VOL | UB VOL | INS A | INS C | INS C-A | BPL A | BPL C | BPL C-A |
|---|---|---|---|---|---|---|---|---|
| 1 | 36088 | 569287 | 81.71 | 84.30 | 2.59 | 13.23 | 10.64 | −2.59 |
| 2 | 29406 | 607146 | 87.61 | 85.60 | −2.01 | 9.00 | 9.67 | .67 |
| 3 | 51662 | 386811 | 77.34 | 78.72 | 1.38 | 15.71 | 14.80 | −.91 |
| 4 | 46324 | 488770 | 78.40 | 81.71 | 3.31 | 12.78 | 12.57 | −.21 |
| 5 | 33993 | 441629 | 85.13 | 83.16 | −1.97 | 9.89 | 11.49 | 1.60 |
| 6 | 28318 | 475208 | 88.77 | 84.63 | −4.14 | 6.32 | 10.40 | 4.08 |
| 7 | 56844 | 366586 | 77.28 | 77.15 | −.13 | 15.83 | 15.97 | .14 |

TABLE IV-continued

IMAGE ANALYSIS VOLUME/WEIGHT METHOD VERSUS WET CHEMISTRY

| SAMPLE | LB VOL | UB VOL | INS A | INS C | INS C-A | BPL A | BPL C | BPL C-A |
|---|---|---|---|---|---|---|---|---|
| 8 | 16774 | 415777 | 87.47 | 86.32 | −1.15 | 9.16 | 9.14 | −.02 |
| 9 | 30231 | 475067 | 84.14 | 84.28 | .14 | 10.80 | 10.66 | −.14 |
| 10 | 32535 | 307897 | 81.06 | 80.84 | −.22 | 14.40 | 13.22 | −1.18 |
| 11 | 40745 | 367956 | 85.96 | 80.45 | −5.51 | 10.51 | 13.51 | 3.00 |
| 12 | 21576 | 438981 | 85.32 | 85.54 | .22 | 11.04 | 9.72 | −1.32 |
| 13 | 32956 | 407562 | 79.60 | 82.84 | 3.24 | 13.54 | 11.73 | −1.81 |
| 14 | 30379 | 506814 | 80.77 | 84.60 | 3.83 | 12.85 | 10.42 | −2.43 |
| 15 | 22838 | 537583 | 85.71 | 86.13 | .42 | 8.10 | 9.28 | 1.18 |

As can be seen from the above tables, the differences between the image analysis of the present invention and those obtained through conventional wet chemistry techniques, (i.e. those values represented by INS B-A, INS C-A, BPL B-A and BPL C-A), are not significant. Thus, the image analysis technique of the present invention accurately determines the concentration of translucent and opaque (quartz and phosphate) components in a phosphate ore stream.

While the invention has been described with reference to particular embodiments, it is understood that various changes may be made without departing from the spirit and scope of the appended claims.

I claim:

1. A method for determining the relative concentrations of translucent and opaque particles present in an ore sample, said method comprising:
    passing a layer of ore particles perpendicularly through a camera viewing plane between said camera and a source of backlighting which comprises in combination a light source for providing diffused background light and a relatively brighter light source for illuminating said ore particles in stroboscopic synchronous accumulation of information by said camera;
    illuminating said ore particles with the background light source and the brighter light source synchronously with the start of frame accumulation in the camera to obtain information representing opaque particles and translucent particles in said layer of ore particles; and
    determining the relative concentrations of translucent and opaque particles in the ore sample.

2. The method of claim 1 comprising:
    illuminating said ore particles and determining relative concentrations of translucent and opaque particles in a plurality of ore particle samples; and
    obtaining an average value of translucent and opaque particle values for the ore.

3. The method of claim 1 further comprising:
    illuminating said ore particles with said background light source and said brighter light source synchronously with the start of frame accumulation in the camera to obtain grayscale values for each pixel captured by the camera which represent opaque particles and translucent particles in said layer of ore particles.

4. The method of claim 3 wherein the determining step comprises:
    determining the relative concentrations of translucent and opaque particles in the ore sample by separating said stored grayscale values into one of three grayscale value ranges representing dark particles representing opaque particles, bright particles representing translucent particles, and intermediate grayscale values representing diffused background light.

5. The method of claim 1 wherein said ore sample comprises phosphate ore.

6. An apparatus for determining the relative concentrations of translucent and opaque particles in a particulate sample, said apparatus comprising:
    a camera capable of capturing an image in frame intervals;
    means for supplying a layer of particles along a path perpendicular to the viewing plane of the camera;
    means for backlighting said layer of particles in synchronization with specified frame intervals of the camera wherein the illumination means comprises in combination a light source for providing diffused background light and a relatively brighter light source for illuminating said ore particles in stroboscopic synchronous accumulation of information by said camera;
    means for storing images captured by the camera; and
    means for calculating the concentration of translucent and opaque materials present in the sample feed stream from the stored images.

7. The apparatus of claim 6 wherein the means for supplying a layer of particles comprises a controlled vibrating feeder.

8. The apparatus of claim 6 wherein the background light source comprises a fiber optic ring illuminator.

9. The apparatus of claim 8 where said background light source comprises a fiber optic flat pack.

10. The apparatus of claim 9 wherein said background light source further comprises a diffuser for light from said fiber optic light pack.

* * * * *